United States Patent
Wei

(10) Patent No.: US 7,169,377 B2
(45) Date of Patent: Jan. 30, 2007

(54) RADIOLIGANDS FOR THE TRP-M8 RECEPTOR AND METHODS THEREWITH

(76) Inventor: Edward T. Wei, 480 Grizzly Peak Blvd., Berkeley, CA (US) 94708

( * ) Notice: Subject to any disclaimer, the term of this patent is extended or adjusted under 35 U.S.C. 154(b) by 222 days.

(21) Appl. No.: 10/687,188

(22) Filed: Oct. 15, 2003

(65) Prior Publication Data

US 2005/0084447 A1 Apr. 21, 2005

(51) Int. Cl.
*A61K 51/00* (2006.01)
*A61M 36/14* (2006.01)

(52) U.S. Cl. .................. 424/1.89; 424/1.11; 424/1.65; 424/1.81; 424/1.85

(58) Field of Classification Search ............... 424/1.11, 424/1.65, 1.81, 1.85, 1.89, 9.1, 9.2
See application file for complete search history.

(56) References Cited

U.S. PATENT DOCUMENTS

| 4,193,936 A | 3/1980 | Watson et al. |
| 4,248,859 A | 2/1981 | Rowsell et al. |
| 4,318,900 A | 3/1982 | Rowsell et al. |
| 5,976,492 A | 11/1999 | Griffiths et al. |
| 6,558,669 B1 | 5/2003 | Govidan et al. |
| 2005/0090514 A1 | 4/2005 | Reynolds et al. |

OTHER PUBLICATIONS

Bernhardt et al, Acta Oncologica 40: 602-608, 2001.
Tsavaler et al., Cancer Research (vol. 61, p. 3760-3769) May 1, 2001.
McKemy et al., Nature 416: 52-58, Mar. 2002.

*Primary Examiner*—Dameron L. Jones

(57) ABSTRACT

One embodiment of the invention is a composition that comprises a radioactive [$^{18}$F], [$^{123}$I], [$^{125}$I], or [$^{131}$I]-N-radiohaloaryl-alkylcarboxamide molecule. The composition binds to the transient receptor potential-M8 (TRP-M8) receptor of cells. The TRP-M8 receptor is selectively expressed in sensory neurons and in malignant tissues such as prostate cancer cells. The [$^{18}$F], [$^{123}$I], [$^{125}$I], or [$^{131}$I]-N-radiohaloaryl-alkylcarboxamide ligand may be used for radioreceptor binding studies, for diagnostic studies, and for radiotherapy of cancerous tissues. Affinity of the [$^{125}$I] or [$^{131}$I]-N-radiohaloaryl-alkylcarboxamide ligand for the TRP-M8 receptor confers selectivity and specificity in delivering lethal radiation to the diseased cells.

11 Claims, No Drawings

RADIOLIGANDS FOR THE TRP-M8 RECEPTOR AND METHODS THEREWITH

BACKGROUND OF THE INVENTION

1. Field of the Invention

This invention generally relates to chemicals that bind to receptors in the TRP (transient receptor potential) ion channel family, more particularly to the subgroup of long TRP (or TRPM) channels, and most particularly to those that specifically bind to the TRP channel called TRP-M8 (trp-p8, $CMR_1$); TRP-M8 receptors are present in sensory nerves and activation of these receptors results in cold sensations. These receptors are also at elevated levels in certain cancers, such as prostate and breast cancer. This invention more particularly relates to TRP binding compositions containing radioactive fluorine and iodine $^{18}F$, $^{123}I$, $^{125}I$, or $^{131}I$, within the molecular structure, said compositions being useful, for example, in radioreceptor, diagnostic imaging, and radiotherapeutic applications.

2. Description of Related Art

About two decades ago a group of scientists discovered novel compounds that have a physiological cooling action on the skin. These were described in U.S. Pat. No. 4,193,936 (Watson et al., Mar. 18, 1980), U.S. Pat. No. 4,248,859 (Rowsell et al, Feb. 3, 1981) and U.S. Pat. No. 4,318,900 (Rowsell, Mar. 9, 1982). Much more recently a new physiological receptor was discovered. This 1104-amino acid protein, deciphered from the cDNA sequence, was named trp-p8 because of its structural homology to receptors of the transient receptor potential (TRP) family. The mRNA for the synthesis of this specific protein was also detected in samples of malignant prostate, mammary gland cells, melanoma, and colorectal cancer cells. The functional role, if any, of TRP-M8 receptors on malignant cells is not known.

The TRP-M8 sequence of the gene/protein was published in Cancer Research (vol. 61, pg. 3760–3769, May 1, 2001. L. Tsavaler, M. H. Shapero, S. Morkowski, and R. Laus: "Trp-p8, a novel prostate-specific gene, is up-regulated in prostate cancer and other malignancies and shares high homology with transient receptor potential calcium channel proteins"). Soon afterwards it was discovered that this receptor was present in sensory neurons and transduced the sensations of cold temperatures (McKemy et al. "Identification of a cold receptor reveals a general role for TRP channels in thermosensation". Nature 416: 52–58, March 2002). Chemicals that elicit sensations of cold, such as menthol and icilin, bind to and activate the cold receptor, as measured by binding constants and by calcium influxes into the cells.

A nomenclature panel composed of experts in the field has recommended the TRP-M8 designation for the cold/prostate receptor because of its structural homology to other protein receptors in this family. However, some still call this receptor trp-p8 or $CMR_1$ (cold-menthol receptor). The tags for the TRP-M8 sequences in the NicePro TrEMBL Database are Q8R405 (mouse TRP-M8), Q8R444 (rat TRP-M8 or $CMR_1$) and Q8TAC3 (human TRP-M8, or trp-p8). The corresponding identity tags in the GenBank are AF4811480 and AY095352 (mouse), AY072788 (rat) and AY090109 (humans).

Various radioactive fluorine and iodine compounds are used in clinical oncology. For example, $^{18}F$ and $^{123}I$ are used in positron emission tomography (PET) and single-photon emission computed tomography (SPECT), respectively, for the imaging, diagnosis and staging of neoplastic disease. $^{125}I$ and $^{131}I$ are used for the treatment of cancer, especially thyroid cancer. Radioiodine compounds in thyroid therapy are remarkably effective because iodine is incorporated specifically into the thyroid hormones (thyroxin and triiodothyronine). Hence, the malignant cells are selectively and specifically targeted, with minimal damage to normal cells and adverse side effects.

Prostate cancer is the most common cancer among men in the United States. There is no universally agreed-upon strategic plan for its diagnosis and management. Brachytherapy, a treatment well known in the art, involves the implantation of radioactive seeds directly into the prostate gland. The radioactive seeds used in brachytherapy may include iodine-125, iodine-131, palladium, radium, iridium, or cesium.

The pharmacological strategy, to bring radio-labeled compounds to specific targets in malignant cells, to improve diagnosis, or to treat certain cancers, is called targeted radiodiagnostics and targeted radiotherapy. New radiofluorinated and radioiodinated compounds useful for these applications are being sought.

BRIEF SUMMARY OF THE INVENTION

In one aspect of the present invention, N-radiohaloaryl-alkylcarboxamide radioligands with specific affinity for the TRP-M8 receptor are provided. These radioactive ligands are useful to study receptor binding (and to identify new drugs that activate the TRP-M8 receptor), to conduct radio-imaging and radiodiagnostics, and should be useful as radioligands for therapy. The radionuclides preferred are $^{18}F$, $^{123}I$ $^{125}I$, or $^{131}I$ although other radionuclides are also contemplated. The inventive [$^{125}I$]-compounds are useful for laboratory tests, called radioreceptor assays. The inventive [$^{18}F$], [$^{123}I$], [$^{131}I$]-compounds are useful for imaging of the tumor cells in vivo bearing this receptor marker, and the [$^{125}I$] or [$^{131}I$]-compounds are further believed potentially useful for targeted radiotherapy.

Among particularly preferred embodiment compositions are those including [$^{123, \ 125, \ or \ 131}I$]-N-(4'-iodo-2'-methylphenyl)-2-isopropyl-5-methylcyclohexanecarboxamide illustrated below as Structure 1.

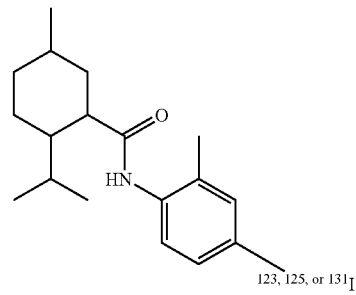

Structure 1

Also among particularly preferred embodiment compositions are those that include [$^{18}F$]-N-(4'-fluoro-2'-hydroxyphenyl)-2-isopropyl-2,3-dimethylbutyramide illustrated as Structure 2.

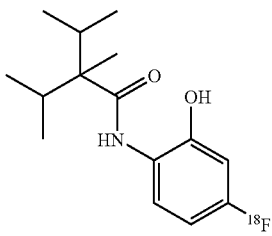

Structure 2

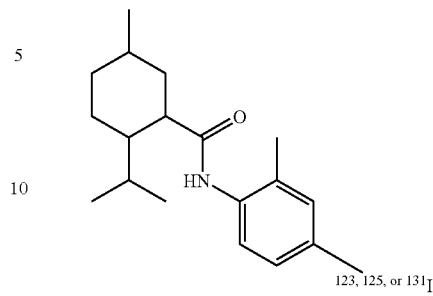

Structure 1

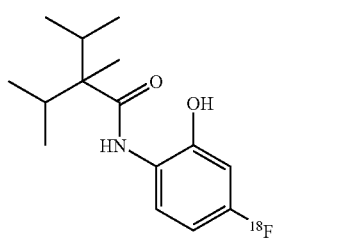

Structure 2

In another aspect of the present invention, a method for using a radioactive ligand comprises providing a N-radiohaloaryl-alkylcarboxamide having a determinable binding for the TRP-M8 receptor and having a specific activity of about 20 Ci/mmol or greater. The provided radioactive ligand is exposed to or contacted with a plurality of TRP-M8 receptors under conditions sufficient to permit specific binding therebetween. Practice of this inventive aspect includes radioreceptor assays, diagnostic imaging and radiotherapy.

Other advantages and aspects of the present invention will be understood by reading the following detailed description and the accompanying claims.

DETAILED DESCRIPTION OF THE INVENTION

Radioligands of the invention preferably have a) a hydrogen bonding site, as exemplified by the CO and NH groups of a carboxamide, b) a hydrophobic group, provided by a branched hydrophobic carbon unit, as exemplified by the cycloalkyl or branched aliphatic groups, and c) an aryl group that can be halogenated. The hydrogen bond/hydrophobic branched carbon units optimize docking into the TRP-M8 binding site and the aryl ring permits delivery of the isotope. The selected isotopes, preferably from the group $^{18}F$, $^{123}I$, $^{125}I$, and $^{131}I$, serve to either mark the location or quantity of the TRP-M8 receptor or to deliver radiation to the TRP-M8 bearing cell.

N-radiohaloaryl-alkylcarboxamides of the present invention can function as ligands for the TRP-M8 receptor and preferably have high affinity to TRP-M8 sites in cells and tissues and a specific activity of about 20 Ci/mmol or greater.

Compositions including the inventive radioligands of the invention have the following applications:

use as ligands for TRP-M8 radioreceptor assays in the laboratory;

use as ligands for diagnosis and imaging of TRP-M8 receptors in prostate tissues and cells; and use as radiotherapeutics (alone or co-administered with local anesthetic amidase inhibitors as potentiators) for prostate disorders such as cancer or benign hyperplasia.

Among preferred embodiment compositions are those comprising a radioactive compound having the structure [$^{18}F$], [$^{123}I$], [$^{125}I$], or [$^{131}I$]-N-radiohaloaryl-alkylcarboxamide, for example: [$^{123, 125\ or\ 131}I$]-N-(4'-iodo-2'-methylphenyl)-2-isopropyl-5-methylcyclohexanecarboxamide, and [$^{18}F$]-N-(4'-fluoro-2'-hydroxyphenyl)-2-isopropyl-2,3-dimethylbutyramide, illustrated below as Structures 1 and 2 respectively.

The term "alkyl" used throughout this description in the context of "N-radiohaloaryl-alkylcarboxamide" is as a generic term to include both acyclic alkyl groups and cycloalkanes. That is, the hydrophobic group is provided by a branched hydrophobic carbon unit, which can be supplied by cycloalkyl or branched aliphatic groups.

Radioactive compounds of the present invention preferably have a specific activity of at least about 20 Ci/mmol, more preferably have a specific activity of at least about 250 Ci/mmol. Radioactive compounds of the invention can function as ligands for the TRP-M8 receptor, and preferably have a Kd for the receptor of about $1 \times 10^{-12}$ to $1 \times 10^{-5}$ molar.

An aspect of the present invention is that the radionuclide (preferably $^{18}F$, $^{123}I$, $^{125}I$ or $^{131}I$) is incorporated (i.e. covalently bound) within the molecular structure of the ligand for the receptor. One advantage of this is that the radiation emitted can readily be detected with radioactivity counters or imaging systems and is directly correlated to high affinity binding to TRP-M8 receptors. Such specific direct radioactive label incorporation into the binding molecule is uncommon and provides excellent results in radioreceptor applications as contemplated in the present invention.

By contrast, a laboratory procedure, for example, the labeling of a binding protein such as a monoclonal antibody by $^{125}I$, carries the risk that the protein will be denatured by the iodine and degraded by enzymes, thereby reducing or destroying its high affinity binding to the receptor target. Moreover, the points of attachment of iodine to the binding molecule are non-specific (see Griffiths et al,. Radioactive iodine labeled proteins for targeted radiotherapy, U.S. Pat. No. 5,976,492, Nov. 2, 1999, herein incorporated by reference).

Incorporating $^{18}F$, $^{123}I$, $^{125}I$ or $^{131}I$ by covalent binding into molecules of the present invention avoids the drawbacks referred to above with radioactive iodine with respect to denaturation, degradation, and potential loss of activity, since incorporation of the radioisotope into the molecule does not significantly change the physical-chemical properties of the molecule. The chemical features of the molecule that determine specificity of binding affinity are retained, with the added property of radiation.

Compounds of the invention are collectively termed "N-radiohaloaryl-alkylcarboxamides".

The endogenous TRP-M8 receptor is a physiological receptor designed to detect temperature changes in its environment and to transmit this signal to the central nervous system so that appropriate regulatory responses can be initiated (e.g. vasoconstriction to reduce heat loss, putting on warmer clothing, avoiding the cold environment). This receptor also responds to drug ligands (e.g., menthol, icilin, certain N-alkylcarboxyl esters and N-alkylcarboxamides) which activate its message transmission system and elicit sensations of cold.

The TRP-M8 receptor on cold sensory nerve endings and on malignant cells, for example in the prostate, are biochemically identical proteins. Thus, the potency of a molecule to elicit cold sensations, for example on the tongue or skin, was used as surrogate index of the binding affinity of the molecule for the TRP-M8 receptor. A number of potent N-substituted-aryl-alkylcarboxamide were synthesized and tested for use as precursors of the inventive compounds and the results are shown in Table 1.

TABLE 1

| CHEMICAL | Cold Sensation Threshold on Tongue*, µg |
|---|---|
| N-(3'-hydroxy-4'-methylphenyl)-2-isopropyl-5-methylcyclohexanecarboxamide | 0.1 |
| N-(4'-methoxyphenyl)-2-isopropyl-5-methylcyclohexanecarboxamide | 0.1 |
| N-(2',4'-dimethylphenyl)-2-isopropyl-5-methylcyclohexanecarboxamide | 0.1 |
| N-(4'-methoxy-2'-methylphenyl)-1-isopropylcycloheptanecarboxamide | 0.2 |
| N-(4'-methylphenyl)-2-isopropyl-5-methylcyclohexanecarboxamide | 0.3 |
| N-(4'-nitrophenyl)-2-isopropyl-5-methylcyclohexanecarboxamide | 0.3 |
| N-(2'-hydroxyphenyl)-2-isopropyl-5-methylcyclohexanecarboxamide | 0.5 |
| N-(4'-fluorophenyl)-2-isopropyl-5-methylcyclohexanecarboxamide | 0.5 |
| N-(4'-methoxyphenyl)-2-isopropyl-2,3-dimethylbutyramide | 0.5 |
| N-(3'-hydroxy-4'-methylphenyl)-1-isopropylcycloheptanecarboxamide | 1 |
| N-(2'-methyl-4'-methoxyphenyl)-3-n-butylbicyclo[2.2.1]hept-5-ene-2-carboxamide | 1 |
| N-(2',4'-dimethoxyphenyl)-3-isobutylbicyclo[2.2.1]hept-5-ene-2-carboxamide | 1 |
| N-(4'-hydroxyphenyl)-2-isopropyl-5-methylcyclohexanecarboxamide | 1 |
| N-(2',4'-dimethylphenyl)-2-isopropyl-2,3-dimethylbutyramide | 1 |
| N-(4'-acetylphenyl)-2-isopropyl-5-methylcyclohexanecarboxamide | 2 |
| N-(4'-methoxyphenyl)-2-isopropyl-2,4-dimethylpentanamide | 2 |
| N-(4'-methylphenyl)-2-isopropyl-5-methylcyclohexanecarboxamide | 3 |
| N-(3',4'-dimethylphenyl)-2-isopropyl-2,3-dimethylbutyramide | 3 |
| N-(4'-methoxyphenyl)-3-isobutylbicyclo[2.2.1]hept-5-ene-2-carboxamide | 4 |
| N-(3'-hydroxy-4'-methoxyphenyl)-3-n-butylbicyclo[2.2.1]hept-5-ene-2-carboximide | 5 |
| N-(3',4'-dimethoxyphenyl)-1-isopropylcycloheptanecarboxamide | 5 |
| N-(4'-ethoxycarboxylphenyl)-2-isopropyl-5-methylcyclohexanecarboxamide | 5 |
| N-(2',5'-dimethylphenyl)-2-isopropyl-2,4-dimethylpentanamide | 5 |
| N-(4'-methoxyphenyl)-1-ethyl-2-methylcycloheptanecarboxamide | 6 |

TABLE 1-continued

| CHEMICAL | Cold Sensation Threshold on Tongue*, µg |
|---|---|
| N-(1'-naphthyl)-2-isopropyl-5-methylcyclohexanecarboxamide | 6 |
| N-(3'-hydroxy-4'-methoxyphenyl)-3-isobutyl-bicyclo[2.2.1]hept-5-ene-2-carboxamide | 8 |
| N-(4'-methoxyphenyl)-1,7,7-trimethylbicyclo[2.2.1]heptane-2-carboxamide | 8 |
| N-(4'-chlorophenyl)-2-isopropyl-5-methylcyclohexanecarboxamide | 8 |
| N-(3'-hydroxyphenyl)-1-isopropylcycloheptanecarboxamide | 10 |
| N-(2',4'-dimethylphenyl)-1-isopropylcycloheptanecarboxamide | 15 |
| N-(3',4'-dimethylphenyl)-1-isopropylcycloheptanecarboxamide | 15 |
| N-(4'-methoxyphenyl)-3-isopropylbicyclo[2.2.1]heptane-2-carboxamide | 15 |
| N-(4'-methoxyphenyl)-3,3-dimethylbicyclo[2.2.1]heptane-2-carboxamide | 20 |
| N-(2',5'-dimethylphenyl)-3,3-dimethylbicyclo[2.2.1]heptane-2-carboxamide | 20 |
| N-phenyl-2-isopropyl-5-methylcyclohexanecarboxamide | 20 |
| N-phenylmethyl-2-isopropyl-5-methylcyclohexanecarboxamide | 20 |

*Filter paper (1 × 1 cm) was impregnated with a known amount of compound and placed on the tongue of the test subject. After 30 sec, the subject was required only to report presence or absence of a cooling effect. Individual sensitivity varied over a considerable range; for example, for 23 subjects, chosen at random, the threshold for a standard such as menthol ranged from 0.02 to 10 µg. Ethoxycarbonyl is $COOC_2H_5$.

Precursor compounds having the desired affinity for the TRP-M8 receptor (such as listed in Table 1) are then radiohalogenated according to standard procedures so as to form inventive comounds for uses in the present invention. The preferred [$^{18}$F], [$^{123}$I], [$^{125}$I], or [$^{131}$I]-N-haloaryl-alkylcarboxamides of the invention are illustrated by Formulas 1 and 2.

Formula 1 is a N-radiohalosubstituted-aryl-cycloalkylcarboxamide or bicycloalkylcarboxamide.

 R—CONH—Y    Formula 1 where (a) R is a saturated or monoethylenically unsaturated alkyl-substituted cyclic or bicyclic alkyl radical containing a total of 7–14 carbon atoms and is selected from the group cyclopentanes, cyclohexanes, cycloheptanes, cyclooctanes, cyclononanes, [3.1.1]bicyclo-heptanes and -hept-5-enes, [2.2.1]bicyclo-heptanes and -hept-5-enes, and [2.2.2]bicyclo-octanes and -oct-5-enes, each alkyl radical containing from 1 to 3 $C_1$–$C_5$ normal or branched alkyl substituents, and (b) Y is a substituted aromatic radical containing substituents $R_1$, $R_2$, and X, wherein $R_1$ is selected from the group hydrogen, hydroxyl, $C_1$–$C_5$ alkyl, $C_1$–$C_3$ alkoxy, $C_1$–$C_3$ carboxyalkyl, $C_1$–$C_3$ oxycarbonylalkyl, $R_2$ is selected from the group hydrogen, hydroxyl, $C_1$–$C_5$ alkyl, $C_1$–$C_3$ alkoxy, trifluoromethyl, nitro, cyano, halo, and X is selected from the group [$^{18}$F]-, [$^{123}$I]-, [$^{125}$I]-, and [$^{131}$I]-.

Preferably, the ring carbon atom to which the carboxamide group is attached carries an alkyl substituent, and/or one of the adjacent ring carbon atoms is alkyl-substituted Examples of cycloalkyls are: 1-isopropylcycloheptyl, 1-isopropylcyclohexyl, 1-isopropyl-2-methylcyclohexyl, 1-isopropyl-2-methylcyclopentyl; 2-isopropyl-5-methylcyclohexyl (p-menthyl), 3-isopropyl-bicyclo[2.2.1]hept-2-yl; and 3-isobutyl-bicyclo[2.2.1]hept-5-en-2-yl.

The carboxamide group is preferably in an equatorial position relative to the plane of the cycloalkyl ring.

Formula 2 comprises a branched chain N-radiohaloaryl-alkylcarboxamide:

R'R''R'''C—CONH—Y      Formula 2 where
(a) R' and R'' are C3 to C5 alkyl (which may be the same or different), and R''' is hydrogen or a C1 to C5 alkyl: where R', R'' and R''' provide a total of at least 5 carbons;
and (b) Y is a substituted aromatic radical having substituents $R_1$, $R_2$, and X, wherein
  $R_1$ is selected from the group hydrogen, hydroxyl, $C_1-C_5$ alkyl, $C_1-C_3$ alkoxy, $C_1-C_3$ carboxyalkyl, $C_1-C_3$ oxycarbonylalkyl,
  $R_2$ is selected from the group hydrogen, hydroxyl, $C_1-C_5$ alkyl, $C_1-C_3$ alkoxy, trifluoromethyl, nitro, cyano, halo, and
  X is selected from the group $[^{18}F]$-, $[^{123}I]$-, $[^{125}I]$-, and $[^{131}I]$-.

Examples of R' and R'' are propyl, isopropyl, butyl, isobutyl, sec-butyl, tert-butyl and pentyl, isopentyl, neopentyl etc. Preferably both R' and R'' are branched alkyl groups, such as isopropyl, isobutyl, sec-butyl, tert-butyl, iso-pentyl. Preferably, R''' is hydrogen, methyl, or ethyl. For branched aliphatics, the carboxamide is attached, for example, to the "3" position of 2,3,4-trimethyl-pentane and 2,4-dimethyl-hexane, and to the "4" position of 3,5-dimethyl-heptane.

The structural features of TRP-M8 binding for N-fluoro- or iodo-aryl-alkylcarboxamides reside principally in the hydrogen bonding CONH moiety and the branched chain hydrophobic carbon unit. The N-substituent can be quite varied; for example, N-ethyl or N-methyl p-menthane-3-carboxamides have oral cooling thresholds as low as 0.2 to 1.1 μg, respectively. In receptor terminology, the N-substituent portion of the molecule is "promiscuous" and many alternatives are permissible to fit the TRP-M8 receptor pocket. Thus, the "Y" of Formulas 1 and 2 can be a substituted aromatic radical, selected from the group phenyl, benzyl, 1-naphthyl, 2-naphthyl, 1-anthracenyl, 2-anthracenyl, 9-anthracenyl, as well as other polyaromatic aromatic rings such as indene, azulene, heptalene, indacene, acenapthlene, fluroene, phenanthrene, and further as well as heterocyclic aromatic rings such as pyridine, dihydropyridine, pyridazine, pyrmidine, pyrazine, indole, purine, indolizine, quinoline, isoquinoline, quinazoline, carbazole, phenazine, phenothiazine, and phenathridine. A polyaromatic ring will also permit multiple halogenation which increases the specific activity of the TRP-M8 ligand and enhances measurement of binding, imaging, and delivery of radiation.

Radiohalogenation of aromatic rings to generate ligands for receptor binding, for radioimaging and for radiotherapy is a chemical technique that is familiar to many practitioners of the art. The preferred isotopes, $^{18}F$, $^{123}I$, $^{125}I$, and $^{131}I$, are most commonly used but it should be noted that alternative therapeutic radionuclides are also contemplated. For example, for targeted radiotherapy for small tumors other halogens such as $^{76}Br$ and $^{77}Br$, and low-energy electron emitters such as $^{58m}Co$, $^{103m}Rh$, $^{119}Sb$, $^{161}Ho$, and $^{189m}Os$ are also feasible (Bernhardt et al. Low-energy electron emitters for targeted radiotherapy for small tumours. Acta Oncologica 40: 602–608, 2001). Radionuclides, such as $^{212}Bi$, $^{213}Bi$ and $^{211}At$, a halogen, which decay by the emission of alpha-particles, can also be incorporated into the N-aryl moiety and are attractive for applications of targeted radiotherapy in accordance with the present invention. The halogens, such as Br and As, may be attached using trialkyl tin reagents and the metal isotopes, such as Sb and Os, may be attached to the ring using metal chelating agents.

Precursor compounds of highest activity and especially preferred for use in the present invention (after modification to incorporate radiohalides) are described in Table 1 and further illustrated by the exemplary preparation of Example 1.

Preparation of Inventive Compounds

The preparation of N-substituted-aryl-alkylcarboxamides is familiar to practitioners of the art of chemistry and, for example, is described in U.S. Pat. No. 4,193,936. Starting with the corresponding alkanoyl chloride, a single step reaction with the appropriate amine yields the desired product. For example, an alicyclic compound, p-menthane-3-carboxylic acid (synonym: 2-isopropyl-5-methylcyclohexanecarboxylic acid) is reacted with thionyl chloride in diethylether to yield the p-menth-3-oyl chloride which, when stirred with the substituted-arylamine at room temperature for about 4 hr, generates the corresponding N-substituted-aryl-p-menthane-3-carboxamide. The precipitated product is readily collected by filtration and may be recrystallized using solvents such ethyl acetate or purified on silica gel columns. The final products are solids stable at room temperature. The arylamine may, for example, be 3-methyl-4-iodo-phenylamine, or 4-fluorophenylamine, or 4-iodo-1-naphthylamine and the corresponding product after reaction with p-menth-3-oyl chloride would be N-(3'-methyl-4'-iodophenyl)-2-isopropyl-5-methylcyclohexane-3-carboxamide, N-(4'-fluorophenyl)-2-isopropyl-5-methylcyclohexane-3-carboxamide, and N-(4'-iodo-1'-naphthyl)-2-isopropyl-5-methylcyclohexane-3-carboxamide respectively.

Synthesis of non-radioactive N-substituted-aryl-alkylcarboxamides as precursors for the inventive compounds are depicted in the following Schematic 1.

Schematic 1

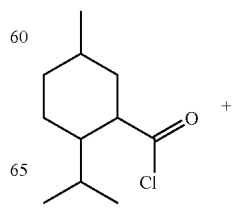

+

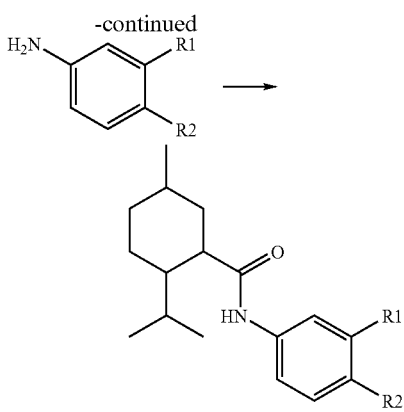

Synthesis of radioactive N-substituted-aryl-alkylcarboxamides useful in practicing the present invention to incorporate a halogen is accomplished with reagents that effect the halogenation process rapidly (because of the short half-life of the isotopes). A standard reagent is trimethyl tin that is bonded to the site of radiohalogenation. Schematic 2 illustrates this halogenation process with trimethyl tin in forming an embodiment of the invention (in which an analog of Structure 1 is formed with $^{18}F$ in place of a radioactive iodine isotope).

Schematic 2

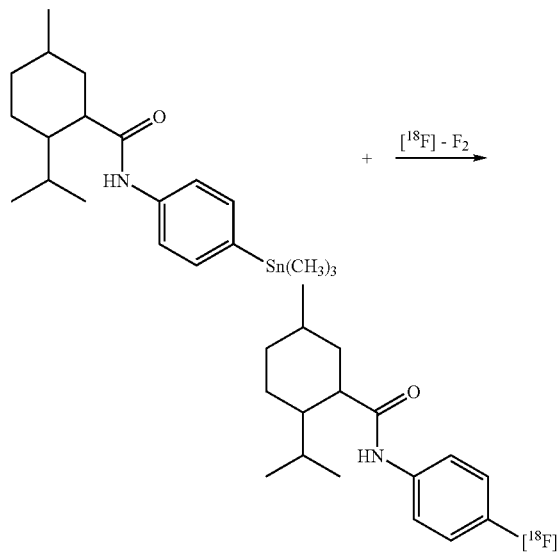

Radioactive Ligands for the TRP-M8 Receptor

The naturally occurring isotope of iodine has an atomic mass of 126.9 Daltons. The radioactive isotopes of iodine are $^{123}I$, $^{125}I$ and $^{131}I$ with half-lives of 13.2 hr, 60.1 days and 8.0 days, and average energy of radioactive emission of 0.159 Mev, 0.02 Mev and 0.36 Mev, respectively. Preparation of [$^{123}I$]-compounds require special facilities because of the short half-life of this isotope. By contrast, $^{125}I$ or $^{131}I$ are inexpensive, readily available at high specific activity of several Ci/matom and obtainable by express mail. Iodine, being a common constituent of the body, has no inherent toxicity in its radioactive form, other than the emitted radiation.

The natural isotope of fluorine has an atomic mass of 19.0. The $^{18}F$-isotope has a half-life of 1.8 hr and an average energy of emission of 0.511 Mev and requires special facilities for preparation. The fluorine compounds used in this invention have no inherent toxicity at the doses employed, other than the emitted radiation.

Amersham Biosciences Corporation (800 Centennial Avenue, Piscataway, N.J. 08855-1327, USA) is a major supplier of reagents for the synthesis of radio-labeled chemicals. Starting materials for [$^{125}I$]- or [$^{131}I$]-compounds can be obtained from Amersham at high specific activities. The isotope half-lives and the average energy of emission dictate the practical use of these labels:

[$^{125}I$]-labeled alkylcarboxamides compounds are useful for radioreceptor assays in the laboratory;

[$^{18}F$]-, [$^{123}I$]- or [$^{131}I$]-labeled N-haloaryl-alkylcarboxamides are useful for scanning or imaging tissues bearing the TRP-M8 receptor; and

[$^{125}I$]- or [$^{131}I$]-labeled N-haloaryl-alkylcarboxamides may be useful for targeted radiotherapy, using fractionated dosages to destroy the desired amount of tissues.

Use of [$^{125}I$]-labeled N-haloaryl-alkylcarboxamides for Receptor Assays

A TRP-M8 receptor has two integral components, an extracellular ligand binding domain that detects the ligand signal and an intracellular domain that is involved in signal transmission. The ligand detection mechanism is structurally specific and analogous to the lock and key model of classical pharmacology. The key is the drug ligand and the lock is the receptor. Signal-transducing receptors are present in small numbers, on the order of a few thousand receptors per cell. Nevertheless, the receptors are designed to regulate crucial cellular functions and therefore become specific targets for drug discovery and development.

To measure drug occupancy of the receptor, pharmacologists use the term "Kd (dissociation constant)" to represent the affinity of the drug to its receptor. The Kd is based on the molar concentration of the drug occupying 50% of the receptor population, so the lower the Kd, the higher the "affinity" or stickiness of the ligand for its receptor. A drug receptor agonist, that is, a drug that elicits a biological response, generally has Kd values in the sub-micromolar ($10^{-6}$), nanomolar ($10^{-9}$) to picomolar ($10^{-12}$) concentration and represents a "high affinity" binding site. Similarly, a drug that binds with high affinity to the receptor, but which does not activate the receptor, may be a high affinity antagonist, preventing the actions of an agonist. To measure Kd for different chemicals, it is necessary to have a primary radioligand that is chemically pure and stable and known to elicit the desired receptor response (for TRP-M8, it can be the sensation of cold, or cation influx into transfected cells that express the receptor). The specific activity of the radioactive ligand must be high enough to detect high affinity binding of the receptor in the tissue being studied. This usually means a specific radioactivity of 30 Ci/mmol or higher.

For example, a synthetic [$^{125}I$]-N-iodoaryl-alkylcarboxamide ligand, such as [$^{125}I$]-N-(4'-iodophenyl)-p-menthane-3-carboxamide (synonym: [$^{125}I$]-N-(4'-iodophenyl)-2-isopropyl-5-methylcyclohexanecarboxamide) is an excellent receptor-assay radioligand. Such a radioligand can be synthesized, for example, at 30 Ci/mmole, which is considerably below the theoretical maximum of 2000 Ci/mmole for [$^{125}I$]-labeled compounds. This ligand can then be used for radioreceptor assays of TRP-M8 agonists, as illustrated by Example 2. A TRP-M8 receptor assay based on [$^{125}$I]-N-iodoaryl-alkylcarboxamide ligand has several applications, as described infra.

Utility of Radio-Labeled -Alkylcarboxamides on TRP-M8 Receptor

An agonist, in pharmacological terminology, is a chemical that activates biological events. The agonist, almost by definition, acts on a specific biological receptor to initiate cellular events. The purpose of a radioreceptor assay is to have methods to identify and measure ligands with low Kd value, and hence high affinity for the desired receptor. Thus, in practice, the first step is the characterization of a prototype [$^{125}$I]-agonist of the TRP-M8 receptor. Once, a prototype has been identified, additional assays of in vitro and in vivo agonist activity are conducted to demonstrate that the binding is functional. These bioassays may also be conducted with non-radioactive alkylcarboxamides to measure the median effective concentrations (EC50). These methods are standard tools in drug screening.

An antagonist, in pharmacological terminology, is a chemical that binds with high affinity to a receptor, occupies it, and prevents the actions of an agonist; but the antagonist itself does not activate biological events. A prototype [$^{125}$I]-agonist of the TRP-M8 receptor can be utilized in screening for a TRP-M8 receptor antagonist. Unknowns can be tested for their ability to displace the [$^{125}$I]-agonist from its binding site. A high affinity antagonist would be a chemical that displaces the [$^{125}$I]-agonist at sub-micromolar concentrations, but by itself does not produce cold sensations.

Carboxamide Radioligands for Laboratory and Diagnostic Applications

The TRP-M8 receptor is exceptional in that its mRNA transcript is found in abundance in biopsy samples of human malignant tissues such as breast cancer, colorectal cancer, melanoma and especially prostate cancer, but not in normal tissues with the exception of prostate epithelial cells (Tsavaler et al., supra). The standard method used for detecting TRP-M8 mRNA transcript in human tissues is to use in situ hybridization techniques with special riboprobes designed to detect the TRP-M8 cDNA. Serial sections of tissues are made, then stained, which enable histopathologists to visually observe any TRP-M8 receptors in the stained tissue. Such methods, however, require advanced laboratory skills and training. More recently, TRP-M8 antibodies have been developed that allow for the detection of TRP-M8 receptor protein on the surface of hyperplastic and malignant in prostate tissues. The use of said antibodies (that is "TRP-M8 immunocytochemistry") has confirmed the presence of TRP-M8 on the surface of human prostate cancer cells.

A [$^{125}$I]-radioreceptor assay in accordance with the present invention, designed to measure the amount and the presence of the TRP-M8 receptor protein in biopsy samples, is potentially a less costly and a more convenient and a more direct alternative than the aforedescribed techniques of in situ hybridization and TRP-M8 immunocytochemistry.

The radioreceptor assay technique has diagnostic applications for patients having cancers that express the TRP-M8 receptor. For example, a biopsy sample of about 10 mg tissue may be homogenized and incubated with a [$^{125}$I]-N-iodoaryl-alkylcarboxamide ligand for 30 min, centrifuged or filtered, dissolved in a solvent, and the beta-emissions counted on a Geiger, scintillation, or other radioactive counter. Based on the findings of Tsavaler et al, supra, one would expect a sharp increase in the amount of TRP-M8 specific binding (Bmax) in malignant tissues, and the relative lower abundance of binding in normal tissues. Such measurements, with small amounts of tissue, because of the sensitivity of a radioreceptor method using a radioligand with high specific activity, can be used, for example, to detect the presence of diseased tissues, to track disease progression, and to measure metastases.

In the laboratory, $^{125}$I is widely used in a technique called autoradiography. Traditionally, $^{125}$I is used to label peptides or proteins in a non-specific location, such as the ring structure of tyrosine and on the ε-amino group of lysine. This technique permits the detection and visualization of receptors or antigens that bind to the labeled agonist or antibody. By the same principles, the [$^{125}$I]-N-iodoaryl-alkylcarboxamide ligand may also be used in accordance with this invention for autoradiographic studies of the TRP-M8 receptor and for discerning its role in hyperplastic and neoplastic processes.

For example, sections of prostate tissues may be incubated with the radioligand, rinsed, and then placed on X-ray film, and the precise sites of TRP-M8 localization mapped by autoradiography. The availability of the [$^{125}$I]-N-iodoaryl-alkylcarboxamide compositions of the present invention should facilitate the study of TRP-M8 expression in hyperplastic and malignant cells and aid in elucidating the role of TRP-M8 in tumor initiation, transformation, invasiveness and metastatic activity.

Radioimaging/Radiodiagnostic Uses of [$^{18}$F], [$^{123}$I], [$^{124}$I] or [$^{131}$I]-N-iodoaryl-alkylcarboxamides with High Affinity for TRP-M8.

Various radioactive fluorine and iodine compounds are used in clinical oncology. For example, $^{18}$F and $^{124}$I are used in positron emission tomography (PET), and $^{123}$I and $^{131}$I in single-photon emission computed tomography (SPECT), respectively, for the imaging, diagnosis and staging of neoplastic disease. The emission of coincident or single high energy photons permits computerized tomography imaging that yields useful information about receptor marker binding, localization, and clearance rates. A useful isotope for PET imaging is $^{18}$F, an isotope with a 110 min half life that generates coincident 511 KeV photons which is measured by PET at a resolution of 0.5 to 1.8 mm at marker concentrations of $10^{-9}$ to $10^{-12}$ M in tissues. A useful isotope for SPECT imaging is $^{123}$I an gamma-emitter with a 13.3 hour half life. Eighty-five percent of the isotope's emissions are 159 KeV photons, which is readily measured by SPECT instrumentation currently in use.

The use of [$^{18}$F]-deoxyglucose PET methods for monitoring the progress of prostate cancer has limited success in part because such prostate cells have limited metabolic activity. A [$^{18}$F]-TRP-M8 ligand, using PET imaging, will have utility as a non-invasive method in staging this disease. $^{124}$I, having a longer half-life of 4.11 days than $^{18}$F can also be used, but it has limited availability. The high resolution of PET can also allow the surgeon to detect metastases, to stage the disease, to assess hormonal sensitivity to androgens, and to gauge the feasibility of tissue removal. Similarly, a [$^{123}$I] and [$^{131}$I]-TRP-M8 ligand can be used for SPECT applications in prostate diseases.

Radiotherapeutic Use of [$^{125}$I] or [$^{131}$I]-N-iodoaryl-alkylcarboxamides with High Affinity for TRP-M8.

The expression of TRP-M8 receptor in tissues of the prostate [Tsavaler et al. supra] makes this receptor a potential target for treatment of benign prostatic hyperplasia. The expression of TRP-M8 receptor in malignant tissues of the prostate, mammary gland and colon, makes this receptor a potential target for cancer radiotherapy. The drug designed for the target must be selective and specific: selective in the sense that hyperplastic or cancer cells express this target more than normal cells, and specific in the sense that the molecular target will have structural features that bind the drug with high affinity. Standard pharmacological strategies for targeting receptors (information described on the Website of Dendreon Corp) expressed in hyperplastic and neoplastic cells are to:

a) make a monoclonal antibody against TRP-M8. The binding of the monoclonal antibody to the receptor leads to cell death, for example, by triggering apoptosis;

b) target a small molecule agonist of TRP-M8 to the receptor to cause excess entry of calcium into cells bearing the TRP-M8 receptor. Calcium levels in cells are tightly regulated, and it may be possible to devise a small molecule to manipulate the TRP-M8 coupled calcium channels in such a manner as to cause cell death; and c) devise an epitope based on the TRP-M8 structure such that the body will develop an antibody response to TRP-M8. An immune system attack against TRP-M8-containing malignant cells may reduce cancer growth.

I contemplate a fourth alternative. A [$^{125}$I] or [$^{131}$I]-N-iodoaryl-alkylcarboxamide agonist or antagonist of the TRP-M8 receptor with high affinity binding for this receptor can be a "letter bomb" for killing cancer cells bearing this receptor. Here, the binding affinity (that is, the address to the receptor) is an innate part of the molecular framework and the radiation from $^{125}$I or $^{131}$I is the lethal message. Unlike the current brachytherapy technique, compounds and compositions of the present invention possess selectivity and specificity to deliver a sophisticated lethal message to a specific target address.

The high specific radioactivity that may be attained with $^{125}$I or $^{131}$I offers tremendous therapeutic advantage if the radiation can be focused on a localized target. Standard doses of oral or intravenous [$^{131}$I]-sodium iodide for the treatment of thyroid malignancy can range from 0.75 to 100 milliCi. As noted earlier, [$^{125}$I] or [$^{131}$I]-alkylcarboxamides may easily be synthesized at a specific activity of 250 Ci/mmol or higher to give a compound with a specific activity of greater than 1 Ci/mg. Injection or oral intake of 0.1 mg of such compounds will yield therapeutic dose of $\geq$100 milliCi. Because this radiation is selectively localized to hyperplastic or malignant cells, normal cells are spared and, I believe desirable therapeutic effects may be achieved.

To carry out such therapeutic applications, the following procedures are contemplated. The anti-tumor activity of a given [$^{125}$I] or [$^{131}$I]-N-iodoaryl-alkylcarboxamide agonist/antagonist of the TRP-M8 receptor is first measured by its cell-inhibiting or anti-proliferative actions (versus the non-radioactive isotope) on cell lines expressing the TRP-M8 receptor. If activity is found with EC50 ranges of between nanomolar to low micromolar concentrations, then the radioactive compound will be tested in mice bearing transplanted tumor cell lines expressing the TRP-M8 receptor. Tumor volume, rate of growth, distant metastases, and histological features of the cancer cells in nude mice will be evaluated using standard techniques that are well known in the art. Pre-clinical in vivo test results from the nude mouse model and other animal models of cancer are the final prelude to clinical evaluation of the drug candidate in humans.

Before a [$^{125}$I] or [$^{131}$I]-N-iodoaryl-alkylcarboxamide agonist/antagonist of TRP-M8 is administered to human cancer patients, the level of TRP-M8 expression in the target tissues preferably is determined. A standard polymerase-chain reaction of the mRNA for the receptor may be used on biopsied tissues. Alternatively, [$^{125}$I]-N-iodoaryl-alkylcarboxamide radioreceptor binding to the biopsied tissues may be measured. Also, the non-radioactive N-iodoaryl-alkylcarboxamide agonist may be tested on the lips of the patient to determine the presence of the cold receptor, although the cutaneous effects of this receptor stimulation may not correlate to levels of TRP-M8 in neoplastic cells.

The N-radioiodoaryl-alkylcarboxamide if administered intravenously is subject to rapid degradation by liver amidases. One way to circumvent this rapid biostransformation is to administer an alternative amide substrate concurrently or just before the radioactive carboxamide. Such substrates may be lidocaine (Xylocaine®) which can be infused at a bolus dose of 50–100 mg over 2 to 3 min and this procedure repeated twice for a total dose of 300 mg in one hr. Another drug in this category is procainamide (Procan®). Procainamide can be given up to 1.5 gm in a 6 hr period. These anti-arrhythmic cardiac drugs are considered relatively non-toxic at these doses and may be ideal for co-administration with radiodiagnostic procedures using [$^{18}$F] or [$^{123}$I]-labeled TRP-M8 drugs or for radiotherapeutic doses of [$^{125}$I] or [$^{131}$I]-labeled TRP-M8 drugs.

Another consideration in administering radiotherapeutic drugs to human cancer patients is that of toxicity. To avoid irradiation of the TRP-M8 receptor in normal tissues, the drug can be delivered locally into the tumor or into the regional circulation of the malignant tissues. If the radioactive drug is to be administered by oral intake or by intravenous injection, it may be possible to protect the TRP-M8 in normal tissues from the radiation by topical or oral administration of the non-radioactive drug. For example, the non-radioactive ligand or a surrogate such as menthol may be administered as a lozenge, in chewing gum, or as a capsule or pill, to protect the mucous lining of the gastrointestinal tract against the radionuclide. Eye-drops and nose-drops containing the non-radioactive ligand may also be administered to protect the TRP-M8 receptors in these tissues. A sulfonamide TRP-M8 agonist may be orally administered to protect the urinary bladder epithelium against the radioactive ligand or its metabolites. In addition, radioprotective drugs such as thiols may be co-administered if the TRP-M8 receptor is present in tissues such as the liver or kidney.

It is well understood in the art of cancer chemotherapy that a single agent may not be sufficient to control the growth and spread of disease. Thus, other agents may be used in combination with the present invention. Also, the precise dosage and duration of treatment is a function of the tissue being treated and can be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

Experimental

EXAMPLE 1

Synthesis of an Exemplary Radioactive N-haloaryl-alkyl-carboxamide

[$^{18}$F], [$^{123}$I], [$^{125}$I], and [$^{131}$I]-N-haloaryl-alkylcarboxamide radioligands of the invention were synthesized, for example, at 25 Ci/mmole. The non-radioactive form of these chemicals are known to be potent and active on the TRP-M8 receptor.

A particularly preferred TRP-M8 receptor ligand embodiment of the present invention, sometimes designated CP-120, is illustrated by Structure 1 where the radioisotope is $^{125}$I. The precursor of this compound is N-(2'-methyl-4'iodophenyl)-2-isopropyl-5-methylcyclohexanecarboxamide. One can readily replace the non-radioactive iodine atom with one of the isotopes $^{123}$I, $^{125}$I, or $^{131}$I, the choice of which depends on the intended use.

CP-120 or its $^{123}$I, $^{131}$I analogs are prepared from the nonradiolabeled trimethyl tin precursor by oxidation with labeled sodium iodide and chloramine-T. The precursor is made from the parent by replacing the iodo group with a trimethyl tin group in the presence of tetrakis (triphenyl phosphine) palladium and bis(trimethyl)tin. The initial non-radiolabeled compound is prepared by reacting 2-isopropyl-5-methylcyclohexane carbonyl chloride with 2-methyl-4-iodo-phenylamine. It should be noted the corresponding $^{18}$F compound may be made by the same technique.

A mixture of N-(2'-methyl-4'iodophenyl)-2-isopropyl-5-methylcyclohexanecarboxamide (500 mg, 1.25 mmol), tetrakis(triphenylphosphine)-palladium (150 mg, 0.13 mmol, 10% molar equivalent), bis(trimethylstannyl) (510 mg, 1.5 mmol), triethylamine (50 ml), and THF (50 ml) was heated at reflux for 12 hr. The reaction mixture was evaporated to dryness in vacuum. The residue was dissolved in ethylacetate and crystallized by the addition of methanol.

Radiochemical synthesis to produce CP-120 used the following method. A THF solution of N-(2'-methyl-4'-trimethylstannylphenyl)-2-isopropyl-5-methylcyclohexanecarboxamide (1 mg/ml) was prepared. To 5 ml of this solution was added Na$^{125}$I (0.5 to 1.0 mCi, 3 to 5 ml) in 0.1 N NaOH, followed by the addition of 0.05 N HCl (10 ml) to adjust to pH 4.0 to 5.5. A freshly prepared solution (1 ml) of chloramine-T (1 mg/ml) was added to the above mixture, and the solution was incubated at room temperature for 15 min. After this time, 20 ml of sodium metabisulfite (3 mg/ml) were added to terminate the reaction, and the solution was incubated for an additional 5 min. Finally, a saturated solution of sodium bicarbonate (50 ml) was added to the reaction vial, and the radioactivity was extracted with chloroform (5 ml). The final product is obtained by HPLC chromatography and used without carrier. For intravenous injection, the trimethyl tin compound is supplied as a sterile ethanolic solution for reaction with radiolabeled NaI and chloramine-T in sterile saline. Unreacted materials are removed simply using a C18 Sep Pak cartridge, yielding CP-120 of more than 98 percent radiochemical purity. This is illustrated by Schematic 3.

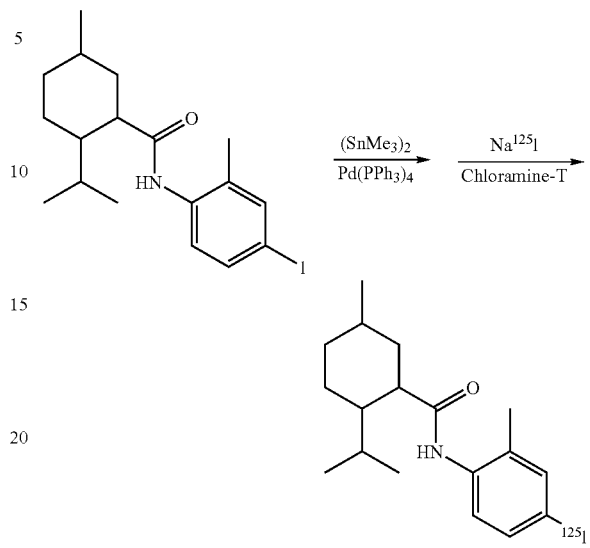

Schematic 3

The incorporation efficiency of radioactivity is nearly quantitative. It should be noted that, in the above synthesis, alkyl or cycloalkyl substituents can be singly added onto the aryl ring using methods well known to the art. The use of trimethyl tin for radio-labeling is only one example of such technology for single addition of halogens, and alternative organometallic reagents are available.

EXAMPLE 2

Radioreceptor Assay

The synthesized radioligand of the invention, such as the [$^{125}$I]-CP-120 prepared as in Example 1, at a specific activity of 25 Ci/mmole, is now used for a radioreceptor assay. In a standard test-tube method for competitive receptor binding, a tissue known to contain the TRP-M8 receptor, such as dorsal root ganglia neuronal cultures or a human prostate cancer cell line, is incubated with [$^{125}$I]-CP-120 until steady-state conditions are reached (usually 30 to 60 minutes). The bound radioactive ligand is then separated from the free radioactive ligand by methods well known in the art such as filtration, centrifugation, dialysis, or size exclusion chromatography. To differentiate between specific (receptor) binding from non-specific binding, a non-radioactive N-haloaryl-alkylcarboxamide, such as N-(4'-methoxy-phenyl)-2-isopropyl-5-methyl-cyclohexanecarboxamide, may be used. After these parameters are established, the next procedure is to conduct a saturation experiment that will establish the Kd and the Bmax (which is the density of receptors in a given tissue and is a pharmacological technique well known in the art). Various concentrations of radioactive ligand are incubated with the receptor preparation and the ratio of the bound and free levels of radioactive ligand is measured. The standard Rosenthal plot or Scatchard analysis of the binding data yields the constants Kd and Bmax.

These and other uses of the present invention will become readily apparent to the skilled artisan once he or she has read the disclosure in this application. It is to be understood that while the invention has been described above in conjunction with preferred specific embodiments, the description and It is claimed:

1. A N-radiohaloaryl-alkylcarboxamide radioligand wherein the alkyl moiety thereof is a cyclohexane radical, the radioligand having a high affinity to TRP-M8 receptors in cells and tissues and having a specific activity of at least about 20 Ci/mmol or greater, wherein the TRP-M8 affinity is characterized by a Kd of about $1\times10^{-5}$ or less.

2. The radioligand as in claim 1 wherein the radiohalo moiety is covalently bound in the molecule.

3. The radioligand as in claim 2 wherein the radiohalo moiety is selected from fluoride and iodide radionuclides.

4. The radioligand as in claim 3 wherein the specific activity is about 250 Ci/mmol or greater.

5. The radioligand as in claim 1 wherein the cyclohexane radical contains from 1 to 3 $C_1$–C5 normal or branched alkyl substituents.

6. The radioligand as in claim 1 wherein the aryl moiety is a substituted aromatic radical represented by Y—, the substituents being represented by $R_1$, $R_2$, and X, wherein $R_1$ is selected from the group hydrogen, hydroxyl, $C_1$–$C_3$ alkoxy, $C_1$–$C_3$ carboxyalkyl, $C_1$–$C_3$ oxycarbonylalkyl, $R_2$ is selected from the group hydrogen, hydroxyl, $C_1$–$C_3$ alkoxy, trifluoromethyl, nitro, cyano, halo, and X is selected from the group [$^{18}$F]-, [$^{123}$I]-, [$^{125}$I]-, and [$^{131}$I]-.

7. A composition comprising a N-radiohaloaryl-alkylcarboxamide of Formula 1:

   Formula 1 where (a) R is a cyclohexane radical containing from 1 to 3 $C_1$–$C_5$ normal or branched alkyl substituents, and (b) Y is a substituted aromatic radical containing substituents $R_1$, $R_2$, and X, wherein $R_1$ is selected from the group hydrogen, hydroxyl, $C_1$–$C_3$ alkoxy, $C_1$–$C_3$ carboxyalkyl, $C_1$–$C_3$ oxycarbonylalkyl, $R_2$ is selected from the group hydrogen, hydroxyl, $C_1$–$C_3$ alkoxy, trifluoromethyl, nitro, cyano, halo, and X is selected from the group [$^{18}$F]-, [$^{123}$I]-, [$^{125}$I]-, and [$^{131}$I]-.

8. The composition as in claim 7 wherein the cyclohexane radical of (a) contains 8–12 carbon atoms and the total number of carbon atoms in the alkyl substituents carbons are from 1 to 5.

9. The composition as in claim 8 wherein the carboxamide group is in an equatorial position relative to the plane of the cyclohexyl ring.

10. The composition as in claim 7 wherein the Formula 1 compound has a specific activity of about 20 Ci/mmol or greater.

11. The composition as in claim 7 wherein the Formula 1 compound is a ligand for the TRP-M8 receptor.

* * * * *